Figure 1:
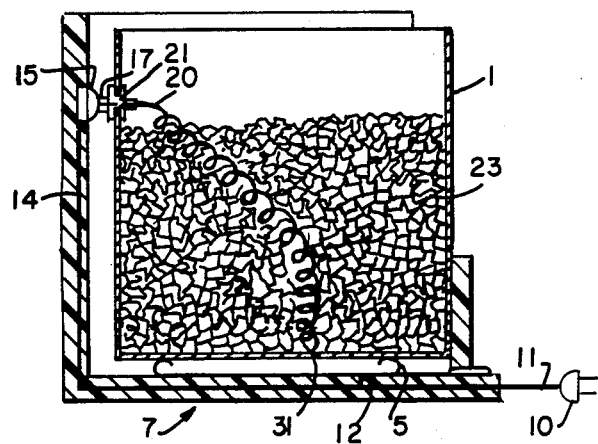
Figure 2:
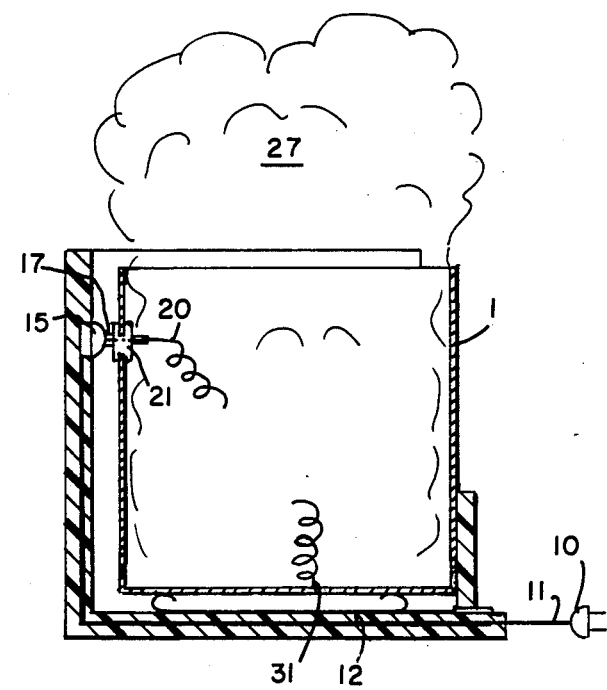

United States Patent [19]

Manchester

[11] Patent Number: 4,777,345
[45] Date of Patent: Oct. 11, 1988

[54] INSECTICIDE DISPENSER CONTAINING FUSIBLE MEMBER

[75] Inventor: Steven T. Manchester, Limerick, Me.

[73] Assignee: GTE Products Corporation, Stamford, Conn.

[21] Appl. No.: 892,610

[22] Filed: Aug. 4, 1986

[51] Int. Cl.$^4$ .............................................. H05B 1/02
[52] U.S. Cl. .................................... 219/271; 239/136; 422/125; 219/275; 219/517
[58] Field of Search ..................................... 239/53–57, 239/34, 60, 136; 219/271–276, 517; 422/305, 125, 1, 28

[56] References Cited

U.S. PATENT DOCUMENTS

| | | | |
|---|---|---|---|
| 1,464,703 | 8/1923 | Fuller | 219/517 X |
| 1,510,409 | 9/1924 | Maybaum | 219/517 X |
| 2,464,633 | 3/1940 | Bohener | 219/517 |
| 2,612,432 | 9/1952 | Boddy | 219/272 X |
| 4,163,038 | 7/1979 | Nishimura et al. | 422/305 X |
| 4,571,485 | 2/1986 | Spector | 239/136 X |
| 4,687,904 | 8/1987 | Melanson et al. | 239/136 X |

Primary Examiner—Andres Kashnikow
Assistant Examiner—Kevin Patrick Weldon
Attorney, Agent, or Firm—James Theodosopoulos

[57] ABSTRACT

An insecticide dispenser capable of setting off a charge of insecticide to fumigate a room and then automatically shutting itself off before the completion of the dispensing of the charge of the insecticide, whereby the dispenser can be safely left unattended during the fumigation of a room. The dispenser includes a container for the insecticide and a fusible member that will break during the volatilization of the insecticide thereby to break the electrical circuit and turn off the power supply.

5 Claims, 1 Drawing Sheet

U.S. Patent    Oct. 11, 1988    4,777,345

INSECTICIDE DISPENSER CONTAINING FUSIBLE MEMBER

FIELD OF THE INVENTION

The present invention relates to electrically heated insecticide dispensers for rooms and particularly to those which are adapted to disperse a charge of insecticide from a container which is to be used only once and in which the insecticide dispenser will shut itself off automatically when the charge has been dispensed.

SUMMARY OF THE PRIOR ART

Insecticide dispensers are well known to the art and devices have previously been introduced which are adapted to dispense insecticides into a room when a container is heated. For example, the U.S. Pat. No. 4,391,781, to van Lit, discloses a resistance heating device that can be utilized with a mat of paper that has been impregnated with an insecticide. The paper strip is urged against the resistance heater so that when the current is turned on, it will dispense the insecticide that is held on the paper. The paper is held against the resistance heating element by a clamp arm that presses the mat against the surface. A depressible lever engages the clamp arm and moves it away from the heating surface thereby releasing the paper strip to facilitate its replacement. In the van Lit patent, however, no disclosure is made of a container of insecticide and the limiting of the dispensing is controlled by the amount of vaporizable material that is held within the paper. No attempt is made in the van Lit patent to shut the resistance heating element off when the vaporizable material has been fully dispensed.

Since the present invention relates to dispensers for insecticides that utilize cannisters which are to be used only once, it is necessary to turn off the resistance heating element when the vaporizable material is fully dispersed into the room. The usual approach for dispensing such vaporizable material is to initiate the vaporization and then quickly leave the room where the dispenser has been disposed. The room is not reentered until quite a while later, when the vapor has settled and is not toxic to the person who is doing the fumigating. If the resistance heater were left on during the entire waiting period, a posibility exists that the dispenser could overheat and cause a fire while it is unattended. Thus, while the van Lit patent may be appropriate for dispensing certain small quantities of volatilizable material, we have found that it is inappropriate for large scale fumigation of entire rooms.

The U.S. Pat. No. 4,202,472, to Lin, discloses the use of a device for bagging trash and simultaneously dispensing insecticides or repellents. The insecticide or repellent is slowly dispensed into the trash to prevent the breeding of micro-organisms. The device does not involve the use of electrical heating for the container and dispenser and thus is not adaptable for use for fumigating a room. The U.S. Pat. No. 4,316,279, to Beacham, discloses a combined container and dispenser for dispensing a volatile product such as an air freshener or insecticide. The invention involves a continuous, low rate dispensing of the volatile product in an ambient atmosphere and is especially not related to the sudden volatilization of large quantities of insecticides such as are contemplated in the present invention. The invention of Beacham is designed to be unobtrusively stuck or hung to a hidden surface so that it is not normally observable by persons nearby whereby the vaporizable material will slowly disperse into the room where it is disposed.

Automated aerosol mist dispensers are disclosed in the U.S. Pat. No. 3,974,941, to Mettler, Patentee discloses a device for injecting short bursts of an atomized liquid such as air fresheners, medicines or insecticides at desired intervals from a spray nozzle in communication with a conventional aerosol can that contains a fluid under pressure. With Mettler's invention, an automated aerosol mist dispenser is disclosed that affords a secure interconnection between the pressurized can of fluid and the control valve mechanism and which is safe against undue leakage, even at relatively high temperatures owing to the provision of a balancing piston feature. No concept, however, is disclosed by Mettler for dispensing a large volume of insecticide into a room in a single charge through the use of a controlled resistance heating element.

U.S. Pat. Nos. 3,151,785, to Scarpa, and 3,466,789, to Kare, involve the use of liquid insecticide dispensers in which the rate of liquid that is being dispensed is controlled through slow dripping of the liquid and subsequent atmospheric volatilization. While Kare may disclose a single dose dispenser for the insecticide, no disclosure is made of electrically heating the dispenser to volatilize its contents.

SUMMARY OF THE INVENTION

According to the present invention, I have discovered an insecticide dispenser that can be electrically heated to dispense the insecticide and then shut itself off automatically. A container that is adapted to hold a mixture of insecticide and a carrier is disposed within a housing. A fusible wire within the container constitutes the heating source. The container is adapted to be part of the electrical circuit and its placement in a housing completes the circuit. The fusible wire which is used heats the charge of carrier-insecticide and will break and shut off the circuit after the volatilization of the insecticide has commenced. With the use of the fusible wire, the dispenser will not overheat when it is left unattended.

As I mentioned above, fumigation of a room involves a person setting up the device and then turning on the power to commence the volatilization of the insecticide. When the heating has commenced, the fumigator promptly leaves the room in which the action has been initiated and closes the door, thereby containing the insecticide within the room and allowing it to do its work. The door is not opened for a significant amount of time so as to prevent poisoning the fumigator. Since it is not desirable to continue heating the container that holds the insecticide for all of the time the fumigator is out of the room because of the possibility of overheating or fire, the dispenser of the present invention is designed to turn itself off by breaking the electrical circuit thereby turning it off and eliminating these possibilities.

The fusible wire is disposed inside of the container and acts as the heater. One end is electrically connected to the inside of the container and is embedded in the charge of insecticide. The other end of the wire is preferably threaded through a sidewall of the container, but insulated therefrom. A contact on the container will slidably engage a contact in the dispenser housing and complete one side of the circuit. A second electrical contact is disposed in the base of the housing and provides a receiver for the container whereby the other side of the circuit is completed. When properly mounted in the housing, the wire threaded through the container will begin to glow and heat the charge of insecticide to initiate the chemical reaction in the carrier. The chemical reaction is self sustaining and once it is commenced, the wire can break without impeding the volatilization of the insecticide. The dispenser can be left unattended for any amount of time since the circuit has been broken and the only heat being produced comes from the volatilization of the insecticide which is self limiting because when the carrier completely reacts, the chemical reaction will end.

DESCRIPTION OF THE DRAWINGS

FIGS. 1 and 2 show an embodiment of the invention. FIG. 1 shows a container holding the mixture of carrier and insecticide disposed in a housing. A fusible wire is disposed in the container and is used as part of the electrical circuit. It will break when the self-sustaining reaction and the volatilization has commenced, as shown in FIG. 2.

DESCRIPTION OF THE PREFERRED EMBODIMENTS

As shown in FIG. 1, an electrically conductive container 1 which is used for the volatilization of the insecticides is disposed in a housing 7. The fusible member 20 that is used to heat the charge of insecticide is strung through the container and is preferably a nichrome or nichrome-based wire. The container 1 rests directly upon exposed electrical contacts 5 and a circuit is established as the exposed contact button 17 engages exposed contact member 15 when the container 1 is properly seated in the housing 7. Preferably, the face of housing 7 is cut away to enable the user to readily seat the container and replace it when the fumigation is complete.

The chemical reaction in the insecticide is initiated by heat which is applied with the nichrome heating element 19 that is electrically connected to the bottom wall of the container 1 at connection 31. Fusible member 20 is insulated from the container 1 at all points, except where it contacts the container 1 at point 31. Insulator 21 insulates the fusible member 20 where it passes through the side wall of container 1. The nichrome wire will begin to glow and will initiate the chemical reaction. As the chemical reaction proceeds, the heating element 20 will become hotter and hotter until it breaks as shown in FIG. 2. At that point, a cloud 27 of insecticide is rising through the room. The fusing of the wire will break the electrical circuit thereby isolating container 1 from the current provided through a conventional plug 10 through line 11. Line 11 forks into two segments, 12 and 14. Segment 12 is connected to contact 5 and segment 14 is connected to button 17. The insecticide dispenser can be safely left in the room since the current is no longer passing through it and the burning of the insecticide and carrier will limit itself by the quantity of insecticide and carrier disposed within container 1. The gauge of the fusible member 20 can be readily established by those with skill in the art and can be selected based upon the quantity of insecticide that is disposed within container 1, its chemical characteristics and the heat necessary to establish the self-propogating reaction.

It is apparent that modifications and changes may be made within the spirit and scope of the present invention. It is my intention, however, only to be limited by the scope of the appended claims.

As my invention I claim:

1. An insecticide dispenser for a room, said dispenser comprising:

a housing and an electrically conductive, non-reuseable container disposed in said housing; and a charge of an insecticide dispersed within a solid carrier, said charge requiring the application of heat to initiate a chemical reaction of the carrier which produces a selfsustaining volatilization of the insecticide upon the application of heat; and first means connecting said container to one side of a power supply; and second means connecting said container to the other side of said power supply, said second means further including an electrically conductive fusible heating means, electrically connected at one end to said container and removably connected at its other end to an electrical contact in said housing, said fusible means being electrically insulated from said container at all points except where it is connected to said container, whereby said fusible means can complete the circuit and initiate the chemical reaction in the charge of insecticide; and said fusible heating means being adapted to break after said chemical reaction has been initiated whereby to discontinue the electrical heating to said charge and permanently disable said container for subsequent reuse.

2. The dispenser according to claim 1 wherein said fusible means extends through an insulator to the outside of said container to an electrical contact surface.

3. The dispenser according to claim 1 wherein said fusible member is a nichrome based wire arranged in said charge and connected to a bottom wall of said container.

4. The dispenser according to claims 1 or 3 wherein an insulator is disposed on the side wall of said container and said fusible means extends through said insulator to the outside thereof to an electrical contact surface.

5. The dispenser according to claims 1 or 3 wherein said contact is disposed on said housing and arranged to engage said contact surface on said container.

* * * * *